United States Patent [19]

Grossman et al.

[11] Patent Number: 5,049,380
[45] Date of Patent: Sep. 17, 1991

[54] ANTI-ALLERGIC EXTRACT

[75] Inventors: Shlomo Grossman, Ramat-Gan; Rina Reznik, Raanana; David Altman, Ramat-Gan, all of Israel

[73] Assignee: Bar-Ilan University, Ramat-Gan, Israel

[21] Appl. No.: 346,104

[22] Filed: May 2, 1989

[51] Int. Cl.$^5$ .................. A61K 35/78; A61K 9/52; A61K 9/22

[52] U.S. Cl. .................. 424/195.1; 424/457; 424/468; 514/825; 514/863; 514/886

[58] Field of Search .............. 424/195.1, 457, 468; 514/825, 863, 886

[56] References Cited

PUBLICATIONS

The Illustrated Herbal, 1987, Crescent Books, New York, New York, 95–96.
Lewis, Medical Botany, p. 391, 1977.
Steinmetz, Codex Vegetabilis, 1957, No. 73, and 689.

*Primary Examiner*—John Rollins
*Attorney, Agent, or Firm*—Irene J. Frangos

[57] ABSTRACT

The present invention describes a novel material which is extractable from plants of the order Malvales and which demonstrates anti-allergic activity.

3 Claims, 5 Drawing Sheets

INHIBITION OF HISTAMINE RELEASE by AA 313

ANTI-ALLERGIC EXTRACT

FIELD OF THE INVENTION

This invention relates to water-extractable plant materials having anti-allergic activity, a process for preparing them and pharmaceutical compositions containing them. More specifically, this invention relates to a material isolated from a plant of the order Malvales, which material is characterized by its anti-allergic activity.

BACKGROUND OF THE INVENTION

The development of allergy in a patient is a complex process. Allergic responses may be effected by antibodymediated (immediate) hypersensitivity, or cell-mediated (delayed) hypersensitivity or a combination of both. Immediate type, or Type I, hypersensitivity reactions result when immunologlobulin E ("IgE") antibodies bind to mast cells or basophils and an allergan (or antigen) binds to that antibody, thus perturbing the cell membrane and triggering a calcium ion influx across the membrane. Microtubule formation and movement of granules to the cell membrane leads to fusion of granule and plasma membrane (degranulation) and release of granule-associated mediators into the intercellular space.

Changes in the cell membrane associated with cell activation, i.e., the calcium influx, activates mast cells both to degranulate and to activate phospholipase A, in parallel. Degranulation releases histamines and hydrolytic enzymes into the system. Activated phospholipase $A_2$ hydrolyzes free arachidonic acid, a fatty acid, which then acts as a substrate for two enzyme systems which form the mediators; for example, leukotrienes and prostaglanins. Prostaglandin $A_2$ and thromboxane $A_2$ (cyclo-oxygenase pathway), and SRS (which is leukotriene $LTC_4+LTD_4$) and chemotactic $LTB_4$ (lipoxygenase pathway) are among the newly synthesized products which result from the metabolysis of the acid. An alternative route independent of phospholipase $A_2$ is believed to lead to the production of histamine, proteolytic enzymes, heparin and chemotactic factors. Of the products of these processes, at least histamine and/or leukotrienes are believed to mediate allergic diseases 5-lipoxygenase acts as a catalyst in the hydrolysis of aracidonic acid to form leukotrienes. Leukotrienes are mediators which are far more active than histamine or prostaglandins. These mediators have potent contractile effects on the respiratory tract. Sneezing and respiratory problems are caused by contractions of smooth muscle of the respiratory tract. Other symptoms are a result of inflammation caused by increased vascular permeability and the attraction of leukocytes. The metabolism of arachidonic acid has been suggested as part of the mechanism of other diseases, i e., rheumatism and psoriasis. 5-lipoxygenase activity may affect these conditions, as well as inflammatory responses.

Allergies have typically been treated by a variety of chemical agents directed toward counteracting their symptoms. Such treatments have only short-term utility and are often accompanied by adverse reactions. For example, antihistamines are often used to alleviate temporarily the general discomfort caused by histamine release. Such drugs, however, cause drowsiness and therefore are often not recommended. Corticosteroids are also used to treat severe allergic reactions. However, these compounds immunosuppress the patient and thereby increase susceptibility to infectious disease. Inhaled salbutamol (or albuterol) is commonly used by asthma patients. However, like other symphathomimetic agents, salbutamol can cause side reactions such as hypertension, angina, vomiting, vertigo, and insomnia.

In view of the disadvantatges of such prior allergy treatments, conventional means for treating allergies remain disappointing to the patient, as well as to the clinician. Therefore, the need exists for a process which avoids these disadvantages and provides effective treatment for allergies, as well as other conditions which result from the metabolism of arachidonic acid.

SUMMARY OF THE INVENTION

It is a principal object of the invention to provide substances suitable for the treatment or prevention of allergic responses. More specifically, this invention relates to pharmaceutically acceptable compounds which are extractable from certain plants and which can be used to treat a mammal to alleviate allergies as well as the symptoms which plague sensitized individuals.

Another object of the invention is to provide substances suitable for the treatment or prevention of allergies, the therapeutic mechanism of which differs in principle from that of the large majority of anti-allergic drugs in use at the present time.

Yet another object of the invention is to provide substances having anti-allergic activity which do not suffer the many disadvantages of conventional anti-allergic (and in particular antihistaminic) drugs.

It is a further object of the invention to provide a relatively simple and economical process for obtaining such substances, when compared with the synthetic processes used to prepare the anti-allergic drugs in current use.

A still further object of the invention is to provide pharmaceutical compositions containing such substances for the treatment of allergies, as well as inflammation, rheumatism and psoriasis.

Without being bound by theory, we believe that suppression of the allergic response in antibody mediated (Type-I) hypersensitivity is due to the direct effect of the described plant tissue extract on the inhibition of 5-lipoxygenase enzymes in activated mast cells. 5-lipoxygenase is the key enzyme in the formation of leukotrienes from the free arachidonic acid released from activated mast cells or basophils. The activated compound seems to act as a free radical scavenger that specifically inhibits the lipoxygenase route of arachidonic acid peroxidation. The fact that all fractions obtained from the active material exhibits strong inhibition of lipoxygenase may indicate that the active components are low molecular weight compounds that exist in the native product as repeating subunits of high molecular weight polymers The present invention, accordingly, provides a material selected from water soluble extracts prepared from plant tissue, and fractions separable from such extracts by chromatography, wherein the tissue is obtained from a plant of order Malvales, and the material is characterized by having anti-allergic activity. In hypersensitive individuals, exposure to an allergen, therefore, will not result in the discomfort, and often danger, caused by the mediators of allergic response. This material also may be used to treat other conditions caused by the metabolism of arachidonic acid; i.e., psoriasis and rheumatism.

According to the present invention, there is also provided a process for preparing an anti-allergic material, which comprises the steps of:

extracting the plant tissue with water;
breaking down the tissue to the extent necessary for the extracting step to be viable; and
separating the aqueous extract from insoluble matter.

In yet another aspect, there is provided in accordance with the present invention a pharmaceutical composition which comprises as active ingredient, an anti-allergic material as described above, together with at least one substance selected from pharmaceutical carriers, diluents, excipients and adjuvents.

DETAILED DESCRIPTION OF THE INVENTION

Figure 1:
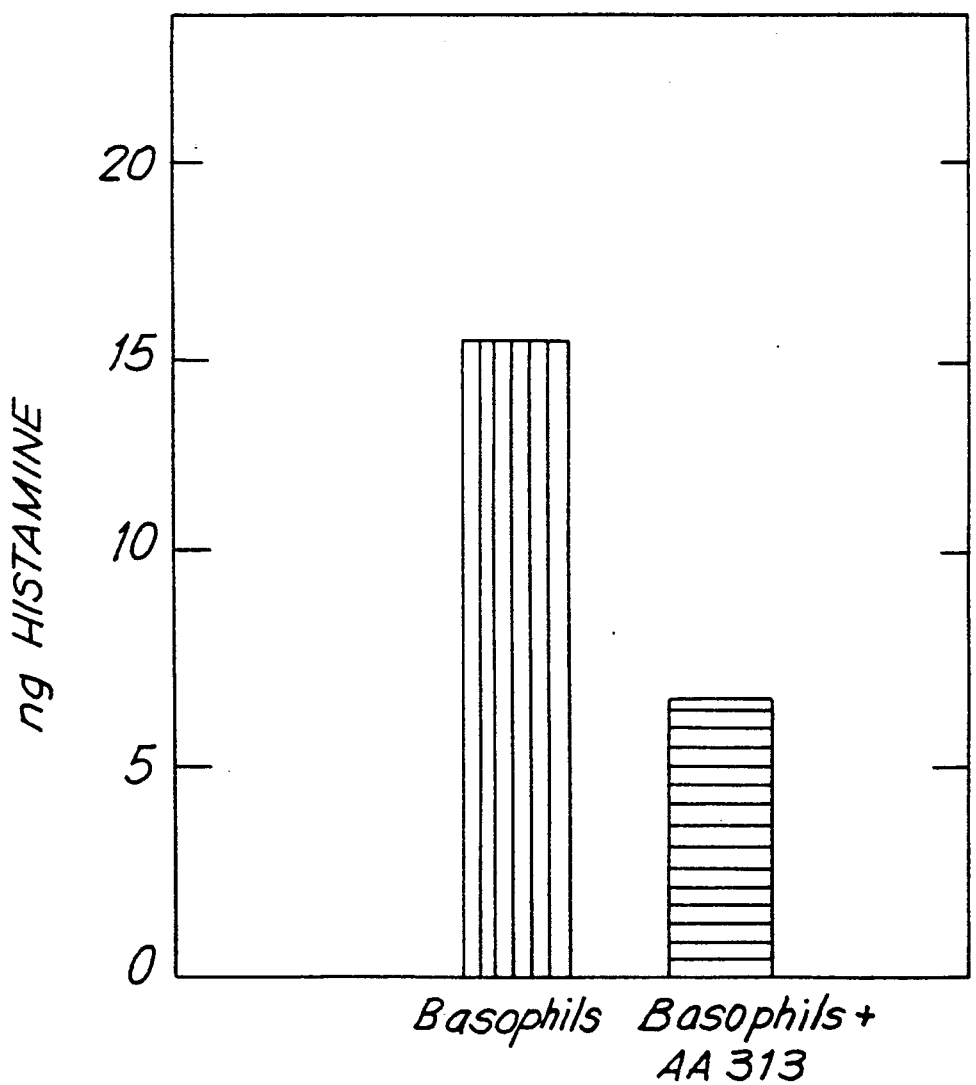
FIG. 1 illustrates inhibition of histamine release by a pharmacologically active material according to the present invention.

As has been mentioned above, the anti-allergic materials of the invention are extractable by water from a plant of the order Malvales. Preferably, there is utilized a member of the family Malvaceae, and more particularly one of the genera Malva, Althaea or Lavatera. The plant tissue may be constituted by fresh leaves and/or stems from these plants.

While in the most general sense, the extractable materials are those which have anti-allergic activity, in a preferred embodiment such materials are further characterized by the fact that they inhibit the formation in vivo of at least one member selected from histamine and the leukotrienes. Most preferably, the extractable materials inhibit the action in vivo of at least one enzyme known to be a link in a chain leading to the formation of the leukotrienes from mast cells or basophils. For example, these materials, in particular, inhibit the action in vivo of 5-lipoxygenase.

Regarding the process of making the material of the invention, each of the stated steps is preferably effected at a temperature within the range of from about 4° to about 100° C., e.g., at ambient temperature, of about 25° C. The breaking down step may for example be effected by mechanical pulverization. In an alternative embodiment, the extracting and breaking down steps may be effected simultaneously by boiling the plant tissue with water.

By way of illustration, the water-soluble active material may be extracted from the plant material using a plant to water ratio in the range of about 0.5:100 to about 1.0:0.5 (w/v), preferably about 2:1 (w/v), after pulverization of the plant material. The pulverization may be carried out at the above-stated temperatures, using a blender, grinding apparatus or any other type of apparatus which will cause fragmentation of the cell walls. The extracted plant material may be separated using filtration, centrifugation, decantation, froth flotation, or any other conventional method used for separating a solid from a liquid.

The crude active material may be used as obtained from the plant, either in dilute form or as an aqueous mixture or as a purified extract. Generally, it is preferred to separate the aqueous extracting medium from the dissolved active material evaporation or lyophilization of the liquid portion to provide a dry, water-soluble product.

As an additional optional step, the separated aqueous extract may be subject to chromatograpic fractionation. In this embodiment of the process, the fractions obtained may be evaluated for anti-allergic activity, and fractions exhibiting high activity may be used as utilized as such.

As previously stated, the separated aqueous extract may be subjected to (e.g.) lyophilization in order to isolate the material substantially free of aqueous extractant.

The present invention also extends to the anti-allergic material, which has been prepared by the process described herein.

The pharmaceutical composition according to the invention may be adapted for (e.g.) oral, parenteral, rectal or topical administration, and it may be in unit dosage form.

Alternatively, the composition may be in a form adapted for slow release in vivo, as is known in the art In yet another alternative, the composition may be adapted for administration by inhalation or insufflation.

The pharmaceutical compositions of the invention may be utilized in conventional type formulations such as, e.g., solutions, syrups, emulsions, injectables, tablets, capsules, suppositories, hydrophilic creams, hydrophilic lotions, hydrophobic creams and hydrophobic lotions. When the formulation is of a type to be administered internally, the active ingredient may be present in an amount such that the composition is suitable for the administration of about 20 to about 500 mg. thereof per kg. weight of a subject.

In order that the invention described herein may be more fully understood, the following examples are set forth. It should be understood that these examples are for illustrative purposes only, and should not be construed as limiting this invention in any way.

EXAMPLE I

Preparation of anti-allergic extract

Figure 3:
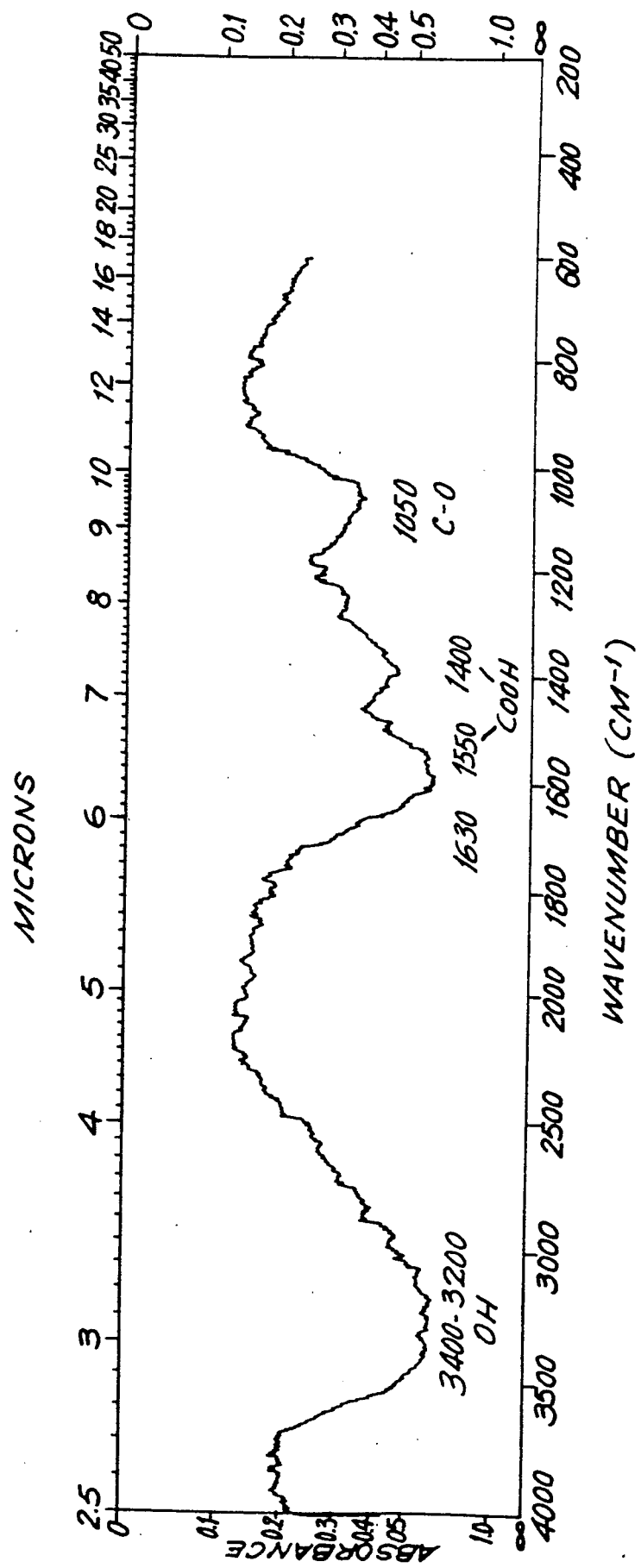
FIG. 3 illustrates the infrared spectra of an aqueous plant extract having anti-allergic properties, in accordance with the invention.

Leaves of Malva were pulverized in a blender with water at 25° C., at a 2:1 (w/v) ratio for 5 minutes. The resulting homogenate was filtered through cheesecloth and then centrifuged at 15000 x g for 10 minutes. The supernatant was collected and lyophilized. The dry material thus obtained was designated AA 313. The same material was obtained by boiling the plant material (not pulverized) with water at 100° C. for 30 minutes. FIG. 3 shows a characteristic infrared spectrum of the crude extract with maxima at 1050 $cm^{-1}$ (C-O); 1400, 1550 and 1620 $cm^{-1}$ (COOH) and 3200 and 3400 $cm^{-1}$ (OH).

We then used this crude extract to test the effect of AA-313 on three indications of the allergic response (a) histamine release, (b) leukotriene formation, and (c) PCA.

(A) Effect of anti-allergic extract on histamine release:

$1 \times 10^6$ fetal cord blood cells, which had been cultured for 21 days and determined to contain 42% basophils, were incubated in 0.5 ml. PBS in presence of $6 \times 10^{-7}$ M A23187 Ca ionophore (California Biochemicals, San Diego) at 37° C. for 25 minutes. AA-313 was added five minutes before the addition of calcium ionophore. Histamine was detected in the supernatants using the fluorimetric assay of Anton and Sayre [P. A. Shore et al., "A method for the fluorometric assay of histamine in tissues," *J. Pharmacol. Exp. Ther.*, 127, pp. 182-96 (1959)].

As shown in FIG. 1, we detected about 15 ng. histamine in our control sample. Only about 7 ng. histamine was produced when 0.1 mg AA 313 was added, after the 21-day culturing step; thus, use of the active material according to the invention resulted in approximately 50% inhibition of histamine release.

(B) Effect of crude anti-allergic extract on leukotriene C4 formation:

A mixture of peripheral blood leukocytes serum (100 ul.) from allergic patients (Anti-"MITE") including IgE, antigen ("MITE") (50 ul. of 10,000 BU/ml) and 0.1 mg AA 313 in Medium 199 were incubated t 37° C. for 2 hours. The mixture was then subjected to HPLC (LT) analysis.

Figure 2:
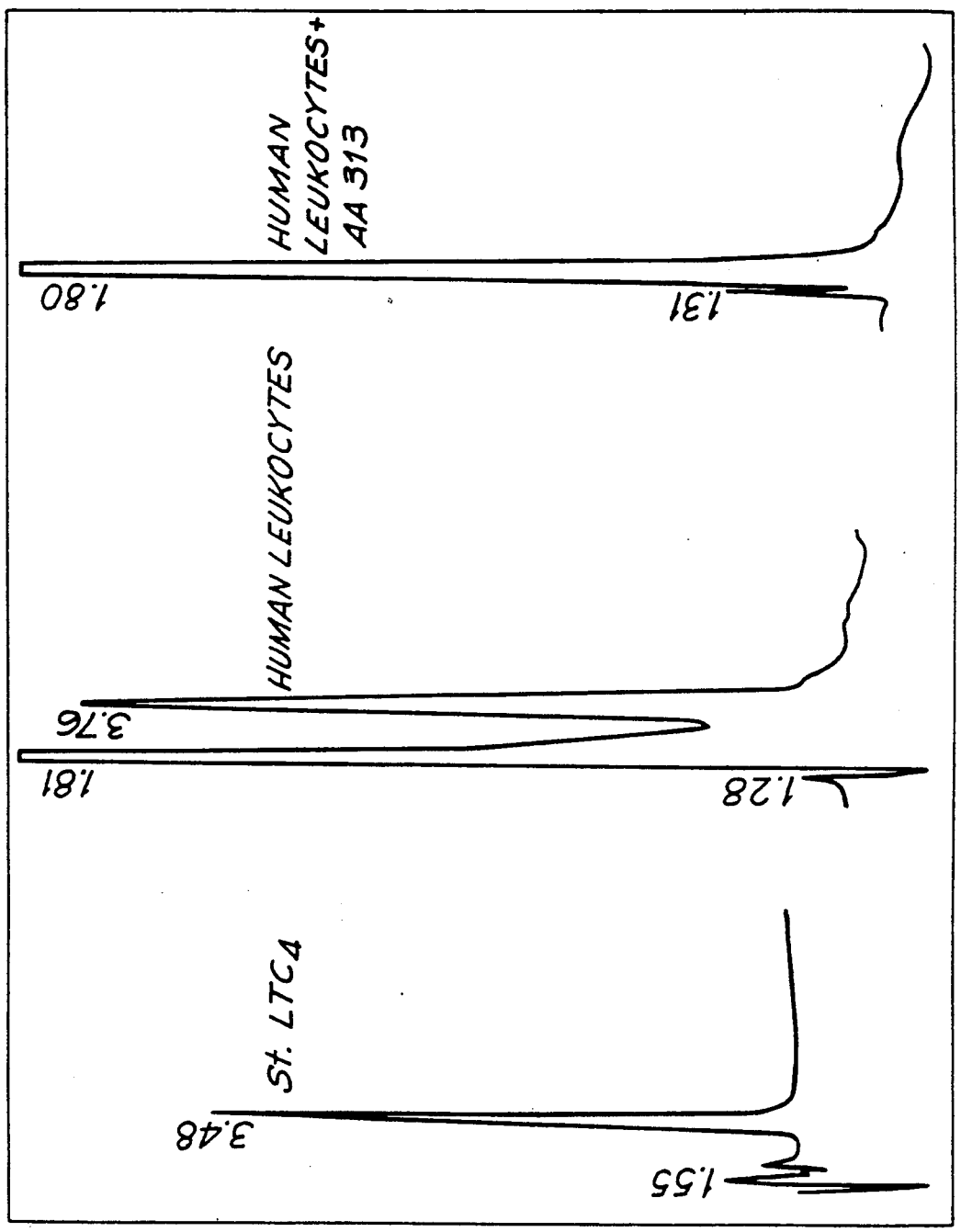
FIG. 2 illustrates inhibition of leukotriene C4 formation by a pharmacologically active material according to the present invention.

We found that the AA 313 had completely inhibited the formation of leukotriene C4 (right hand graph in FIG. 2). This result contrasts with the left-hand and central graphs in FIG. 2, which demonstrates the formation of leukotriene C4 under standard conditions (peak at 3.48) and in presence of human leukocytes (peak at 3.76), respectively.

(C) Inhibition of 5-lipoxyganase by anti-allergic extract

A reaction mixture containing 1050 units potato 5-lipoxygenase was subjected to the action of the known inhibitor caffeic acid as well as to 2 mg AA 313. Enzyme activity was tested by the ability of a sample of the reaction mixture to oxidize arachidonic acid (concentration of 0.33 mM).

As shown in the following table, AA 313 inhibited the enzyme to approximately the same extent as caffeic acid. Enzyme activity was estimated polarographically.

| Inhibitor | Amount | Enzyme activity (units) | % Inhibition |
|---|---|---|---|
| control | — | 1050 | — |
| caffeic acid | 0.33 mM** | 375 | 64 |
| AA 313 | 2 mg. | 405 | 61 |

**final concentration (D) Inhibition of allergic reaction in animals (passive cutaneous anaphylaxis).

According to the assay of I. Roitt, J. Brostoff and D. Male [Immunology, Gower Medical Publishing, p 19.3 (1987)], rats injected intradermally with test serum become sensitized when the IgE binds to mast cells. After 4 hours, the antigen and Evans blue (dye) were injected intravenously; the antigen triggers degranulation and mediator release at the site of the first injection causing locally increased vascular permeability and extravasation of the dye. The skin of the animal was examined after a further 0.5 hour: the area of dye in the dermis being a measure of the amount of antigen-specific IgE present in the original injection.

We tested the effect of AA-313 in this assay, using anti-chicken egg IgE, and egg albumin as the antigen. The active material was supplied freely to the rats: 1 mg./ml. in the drinking water, for a period of two weeks preceding the experimental assay. No dye was found on the surface of the skin, thus showing complete inhibition of the allergic reaction. On the other hand, the control group which were given only water for two weeks, showed large areas of dye on the surface of the skin.

EXAMPLE II

We repeated the series of experiments set forth in Example I, using fractions of AA-313 obtained by filtration. Again we tested the material for its effect on histamine and leukotriene release and PCA.

(A) Histamine Production.

To study the effect of AA-313 on an allergic model in vitro, we took peripheral blood leukocyte cells at a concentration of $10^6$ and added 100 ul of serum of allergic patients which contains anti-mite antibodies. We then added 50 ul of mite antigen, followed by the addition of 1.1 mg of AA-313. This sytem was incubated on a buffered solution for 2 hours at 37° C. As a control, a similar system, without the addition of the AA-313, was incubated. After 15 min. the reaction was terminated and products were extracted with methanol.

Figure 4:
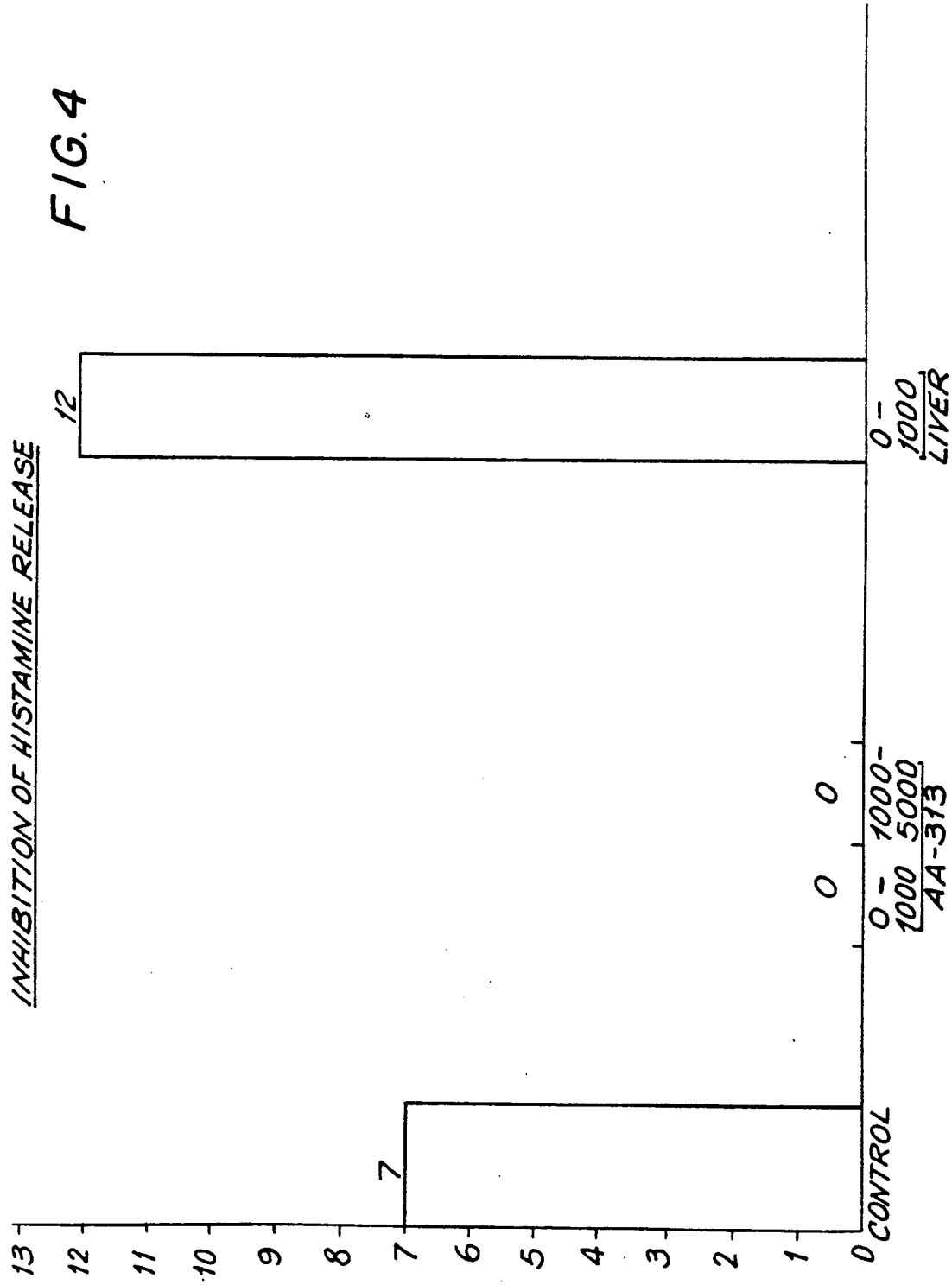
FIG. 4 depicts the ability of AA-313 to inhibit histamine release, in comparison with controls, including liver extract.

The effect of fractions separated from crude extracts on release of histamine is shown in FIG. 4. The fractions with molecular weight of 0-1000, and 1000-5000 from AA-313 and beet exhibited total inhibition of histamine releases. Our control, low molecular fractions (0-1000) separated from liver, did not inhibit the histamine release.

(B) Lipoxygenase Assay (1) Purification of lipoxygenase from potato tubers:

All procedures were carried out at 4° C. unless otherwise noted using the procedures set forth in E. Mulliez and J. P. Lebbome, *Biochem. Biophys. Acta*, 916, pp. 13-23 (1987). [See generally, E. J. Corey and P. J. Lansbury, "Stereochemical course of 5-lipoxygenation of arachidonic acid by rat basophilic leukemia cell (RBL-1) and potato enzyme," *J. Amer. Soc.*, 105, p. 4093 (1983).]

Extraction of enzyme and ammonium sulfate fractionation: Potato tubers (500 g) were homogenized for 3 min. in a Waring Blender under $H_2$ with 300 ml of 0.1u acetate buffer (PH=4.5) containing 2 mu ascorbic acid and 2 mu $NaS_2O_2$. Then the homogenate was filtered through 4 layers of gauze and centrifuged at 15000 g for 20 min.

The supernatant (crude extract) was brought to 25% saturation by solid $(NH_4)_2SO_4$. The precipitate was removed by centrifugation, then the supernatant was made to 50% saturation with respect to $(NH_4)_2SO_2$. The precipitate obtained by centrifugation was dissolved in and dialysed overnight against 50 mu phosphate buffer PH(6.8).

(2) 5-lipoxygenase assays:

Polarographic method: Using this method, the rate of oxygen consumption during the enzymatic reaction was recorded. The assay was performed by the method of S. Grossman et al. [*Phytochemistry*, 8, pp. 2287-93 (1969)] using a YSI Biological Oxygen Monitor (Yellow Instruments CO., Yellow Spring, Ohio). The oxygen monitor contains a Clark electrode in a closed chamber thermostated at the requisite temperature (usually 35° C.). Each chamber contains a magnetic fleas agitated from below by a submersible magnetic stirrer. The reaction mixture (3 ml) contained 15 ul $O_2$ which was considered as 100% $O_2$. A volume of 2.5 ml of buffered linoleate solution (7.5 mM) containing Tween 20 (prepared as described in 2.2.1A) was placed in the reaction cell. The reaction was initiated by adding 0.5 ml of enzyme solution and the oxygen uptake was recorded. The activity was calculated from the initial rate of oxygen absorption and was followed for 1 to 5 min. (depending on the activity of the sample). The results were calculated as nmole (or microliters) of oxygen absorbed per minute by milliliter (or milligram) of enzyme. For blank measurement, the reaction mixture contained 0.5 ml of distilled water or 0.5 ml of denatured enzyme solution (100° C. for 10 min.).

Figure 5:
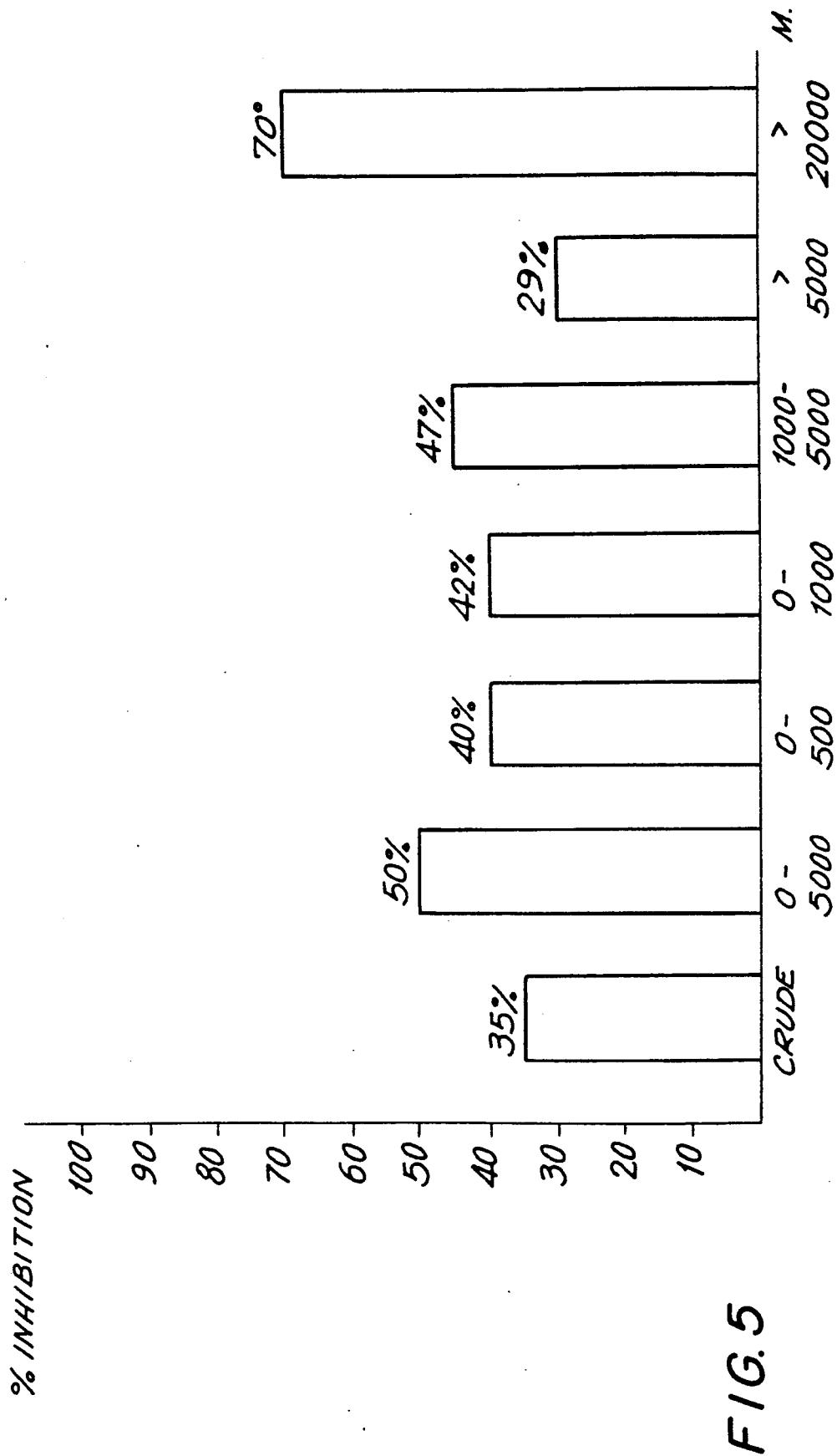
FIG. 5 depicts a comparison of the relative abilities of certain fractions of AA-313 to inhibit 5-lipoxygenase.

(3) Results:

Crude extracts of AA-313 and fractions separated by molecular filters (using Amicon unit) were tested as inhibitors of the 5-lipoxygenase enzyme. The inhibition pattern obtained is described in FIG. 5.

We observed that AA-313 (crude extracts and fractions) significantly inhibited the arachidonic acid peroxidation by 5-lipoxygenase (FIG. 4). On the other hand, rat liver extract and the separated fractions did not exhibit any inhibitory effect on 5-lipoxygenase (results not shown).

(C) Passive cutaneous anaphylaxis (PCA).

We repeated the PCA experiment, shown in Example I (D) with crude extract, using a fraction of AA-313.

A mouse was injected intradermally with IgE (Anti-chicken egg albumin) one week after the compounds were dosed orally (1 mg/1 ml), 6 hours after the injection, 0.1 ml of the antigen (1 mg/1 ml) and a evans blue dye (1 mg/1 ml) were injected intravenously. The antigen triggers degranulation and mediator release at the site of the first injection causing locally increased vascular permeability and extravasation of the dye.

Our results showed that the AA-313 inhibited the response and there was no sign of the dye on the animals treated with this fraction, while our controls were stained blue.

EXAMPLE III

Lethal dose evaluation

Using standard procedures, the $LD_{50}$ in BALB/C mice was found to be about 1.6 g./kg for the extract in dry powder form. 1.6 g./kg. injected IP. Our results are set forth in the table below:

| | THE TOXICITY OF AA313 $LD_{50}$ | | | | | | | | |
|---|---|---|---|---|---|---|---|---|---|
| Expt | #1 | | | #2 | | | #3 | | |
| # Mice | 3 | 2 | 2 | 2 | 2 | 2 | 2 | 2 | 2 |
| AA313 (Dose ug) | 100 | 50 | 10 | 75 | 50 | 25 | 75 | 50 | 25 |
| Mortality | 3 | 1 | 0 | 1 | 1 | 0 | 2 | 1 | 0 |

EXAMPLE IV

Treatment of skin allergy in a patient

An adolescent female patient exhibited intense facial eczema from allergic drug reaction. After attempting alleviation by conventional methods without success, the crude aqueous extract prepared as in Example I by boiling was applied morning and evening AA-313 (0.1%) was administered as a suspension in a commercially available lotion. After two weeks the allergic symptoms had completely disappeared.

While certain embodiments of the invention have been particularly described, it will be apparent to those skilled in the art that many modifications and variations may be made. Therefore, the present invention is not to be construed as limited by any of the particular embodiments shown, rather its scope will be defined only by the claims which follow.

We claim:

1. A method of treating allergies in mammals comprising administering a pharmaceutically effective amount of a material selected from water soluble extracts prepared by extracting plant tissue of the Order Malvales comprising fresh leaves or stems or both, and fractions separable from said extract in water, breaking down said plant tissue to the extent necessary for the extracting step to be viable, separating the aqueous extract from insoluble matter, subjecting said separated aqueous extract to chromatographic fractionation, filtration, or lyophilization, said material characterized by having anti-allergic activity in mammals.

2. A method of treating psoriasis in mammals comprising administering a pharmaceutically effective amount of a material selected from water soluble extracts prepared by extracting plant tissue of the Order Malvales comprising fresh leaves or stems or both, and fractions separable from said extract in water, breaking down said plant tissue to the extent necessary for the extracting step to be viable, separating the aqueous extract from insoluble matter, subjecting said separated aqueous extract to chromatographic fractionation, filtration, or lyophilization, said material characterized by having anti-allergic activity in mammals.

3. A method of treating rheumatism in mammals comprising administering a pharmaceutically effective amount of a material selected from water soluble extracts prepared by extracting plant tissue of the Order Malvales comprising fresh leaves or stems or both, and fractions separable from said extract in water, breaking down said plant tissue to the extent necessary for the extracting step to be viable, separating the aqueous extract from insoluble matter, subjecting said separated aqueous extract to chromatographic fractionation, filtration, or lyophilization, said material characterized by having anti-allergic activity in mammals.

* * * * *